US011224725B2

(12) United States Patent
Pedersen et al.

(10) Patent No.: US 11,224,725 B2
(45) Date of Patent: Jan. 18, 2022

(54) TRANSSEPTAL GUIDE WIRE PUNCTURE SYSTEM

(71) Applicant: Baylis Medical Company Inc., Montreal (CA)

(72) Inventors: Wesley Robert Pedersen, Minneapolis, MN (US); Paul Sorajja, Minneapolis, MN (US)

(73) Assignee: Baylis Medical Company Inc., Mississauga (CA)

( * ) Notice: Subject to any disclaimer, the term of this patent is extended or adjusted under 35 U.S.C. 154(b) by 0 days.

(21) Appl. No.: 16/209,426

(22) Filed: Dec. 4, 2018

(65) Prior Publication Data
US 2019/0167305 A1 Jun. 6, 2019

Related U.S. Application Data

(60) Provisional application No. 62/594,756, filed on Dec. 5, 2017.

(51) Int. Cl.
*A61M 25/09* (2006.01)
*A61B 17/34* (2006.01)
(Continued)

(52) U.S. Cl.
CPC ......... *A61M 25/09* (2013.01); *A61B 17/3468* (2013.01); *A61B 17/3478* (2013.01);
(Continued)

(58) Field of Classification Search
CPC ............ A61B 17/3478; A61B 17/3468; A61B 2017/00247; A61B 2017/00867;
(Continued)

(56) References Cited

U.S. PATENT DOCUMENTS 5,476,498 A * 12/1995 Ayers .................. A61N 1/0563
607/122
7,320,695 B2 1/2008 Carroll
(Continued)

FOREIGN PATENT DOCUMENTS

WO 2009112062 A1 9/2009
WO 2013/101632 7/2013
(Continued)

OTHER PUBLICATIONS

Babaliaros, V.C. et al., "Emerging applications for transseptal left heart catheterization," (2008) J. American College of Cardiology, 51(22):2116-2122.
(Continued)

*Primary Examiner* — Jing Rui Ou
(74) *Attorney, Agent, or Firm* — Vincent Man; Samuel Tekie; Glenn Arnold (57) ABSTRACT

A trans-atrial septal catheter system for delivery of a steerable sheath into the left atrium contains three components. The first component is a three-segmented needle-guide wire composed of a distal needle designed to flex sharply in relation to the conjoined looped guide wire segment after fossa ovalis puncture and needle advancement. The distal guide wire loops are advanced into the left atrium maintaining the angled needle in a central location relevant to the loops for preserving an atraumatic position while stabilizing the loops in the left atrium. The elongated proximal extra stiff guide wire segment is conjoined to the looped segment which crosses the fossa ovalis and extends proximally to become externalized to the femoral vein. This segment is extra stiff and significantly elongated to permit catheter and device exchanges. The guide wire serves as a support rail over which the dilator and sheath can be advanced into the left atrium. This transseptal system is uniquely forward looking and permits cautious and iterative delivery of the
(Continued)

dilator into the fossa ovalis for "tenting" by way of a proximal sheath activator that interacts with the dilator. The proximal externalized GW is then advanced to permit puncture of the fossa ovalis. After puncturing a precise location of the fossa ovalis, the needle and coiled guide wire loops are further advanced into the left atrium. With the proximal activator, the dilator is advanced across the fossa ovalis into the left atrium using single-handed maneuvering for separate dilator advancement and steering of the sheath by way of turning or actuating the sheath handle.

17 Claims, 6 Drawing Sheets

(51) Int. Cl.
  *A61B 17/00* (2006.01)
  *A61B 17/22* (2006.01)
(52) U.S. Cl.
  CPC .......... *A61M 25/09041* (2013.01); *A61B 2017/00247* (2013.01); *A61B 2017/00278* (2013.01); *A61B 2017/00853* (2013.01); *A61B 2017/00867* (2013.01); *A61B 2017/22042* (2013.01); *A61M 2025/09141* (2013.01); *A61M 2025/09175* (2013.01); *A61M 2210/122* (2013.01)
(58) Field of Classification Search
  CPC ...... A61M 25/09041; A61M 2210/122; A61M 2025/09058; A61M 2025/09183
  See application file for complete search history.

(56) References Cited

U.S. PATENT DOCUMENTS

| | | | |
|---|---|---|---|
| 7,635,353 B2 | 12/2009 | Gurusamy et al. | |
| 7,666,203 B2 | 2/2010 | Chanduszko et al. | |
| 7,963,947 B2 | 6/2011 | Kurth et al. | |
| 8,029,470 B2 | 10/2011 | Whiting et al. | |
| 8,114,110 B2 | 2/2012 | Bednarek et al. | |
| 8,157,829 B2 | 4/2012 | Chanduszko et al. | |
| 8,292,910 B2 * | 10/2012 | Chanduszko | A61B 17/0057 606/185 |
| 8,317,810 B2 | 11/2012 | Stangenes et al. | |
| 8,337,518 B2 | 12/2012 | Nance et al. | |
| 8,500,697 B2 | 8/2013 | Kurth et al. | |
| 8,768,433 B2 | 7/2014 | Jenkins et al. | |
| 8,900,193 B2 | 12/2014 | Paul et al. | |
| 8,900,214 B2 | 12/2014 | Nance et al. | |
| 8,986,264 B2 | 3/2015 | Kimmel et al. | |
| 8,992,556 B2 | 3/2015 | Chanduszko et al. | |
| 9,162,037 B2 | 10/2015 | Belson et al. | |
| 9,326,756 B2 | 5/2016 | Stangenes et al. | |
| 9,358,039 B2 | 6/2016 | Kimmel et al. | |
| 9,533,120 B1 | 1/2017 | Kimmel et al. | |
| 9,585,692 B2 | 3/2017 | Kurth et al. | |
| 9,700,351 B2 | 7/2017 | Maisano et al. | |
| 9,717,523 B2 | 8/2017 | Feng et al. | |
| 2004/0073110 A1* | 4/2004 | Stewart | A61B 5/1076 600/437 |
| 2004/0073141 A1* | 4/2004 | Hartley | A61M 25/09 600/585 |
| 2004/0129352 A1* | 7/2004 | Shiota | A61M 25/09 148/527 |
| 2005/0065507 A1* | 3/2005 | Hartley | A61B 18/1492 606/41 |
| 2005/0101984 A1* | 5/2005 | Chanduszko | A61B 17/0057 606/185 |
| 2007/0005019 A1* | 1/2007 | Okishige | A61B 17/3478 604/175 |
| 2007/0088355 A9 | 4/2007 | Auth et al. | |
| 2007/0173878 A1* | 7/2007 | Heuser | A61B 17/11 606/185 |
| 2008/0125802 A1 | 5/2008 | Carroll | |
| 2009/0105654 A1* | 4/2009 | Kurth | A61M 25/09 604/170.03 |
| 2009/0105742 A1* | 4/2009 | Kurth | A61M 25/09 606/185 |
| 2011/0087261 A1 | 4/2011 | Wittkampf et al. | |
| 2012/0035590 A1* | 2/2012 | Whiting | A61B 17/3468 604/528 |
| 2014/0188108 A1 | 7/2014 | Goodine et al. | |
| 2014/0371676 A1 | 12/2014 | Leeflang et al. | |
| 2015/0173794 A1* | 6/2015 | Kurth | A61M 25/09 600/585 |
| 2016/0022962 A1 | 1/2016 | Beissel et al. | |
| 2016/0089180 A1 | 3/2016 | Entabi | |
| 2016/0175009 A1* | 6/2016 | Davies | A61B 17/3478 606/47 |
| 2017/0189113 A1 | 7/2017 | Urbanski et al. | |
| 2017/0296781 A1 | 10/2017 | Sapir et al. | |
| 2018/0168687 A1* | 6/2018 | Drake | A61M 25/0662 |
| 2019/0015644 A1 | 1/2019 | Smith et al. | |

FOREIGN PATENT DOCUMENTS

| | | |
|---|---|---|
| WO | 2015019132 A1 | 2/2015 |
| WO | 2020223230 A1 | 11/2020 |

OTHER PUBLICATIONS

Earley, M.J., "How to perform a transseptal puncture," (2009) Heart, 95:85-92. doi:10.1136/hrt.2007.135939, Downloaded from heart.bmj.com on Jun. 16, 2009.
PCT International Search Report dated Apr. 25, 2019 in application No. PCT/US2018/063815.
PCT Written Opinion dated Apr. 25, 2019 in application No. PCT/US2018/063815.
PCT International Search Report dated Aug. 27, 2020 in PCT/US2020/030264, filed Apr. 28, 2020.
PCT Written Opinion dated Aug. 27, 2020 in PCT/US2020/030264, filed Apr. 28, 2020.
PCT Demand and Amendments under Article 34 filed Feb. 24, 2021 in PCT application No. PCT/US2020/030264.
PCT International Preliminary Report on Patentability dated Jun. 7, 2021 in PCT application No. PCT/US2020/030264.

* cited by examiner

TRANSSEPTAL GUIDE WIRE PUNCTURE SYSTEM

FIELD OF THE INVENTION

The present invention is directed to a system for performing intracardiac transseptal puncture and guide wire access to left heart structures. More specifically, the present invention is directed to achieving transseptal puncture in a highly efficient and safe manner both to gain access to the left atrium by way of a distal needle segment, and mid-looped or coiled left-atrial segment and linear elongated proximal segments. It serves as a platform for structural or other device delivery to the left atrium in the heart. A uniquely configured steerable sheath and dilator may be incorporated with this needle-guide wire. Alternatively, it can be used with most commercially available dilator-sheath transseptal catheter systems.

BACKGROUND

Transseptal punctures are generally used to access the left atrium (LA) of the heart by way of the right atrium (RA). Access to the LA is commonly required for atrial fibrillation ablation and, more recently, treatment of valvular and other structural heart diseases. The current transseptal device(s) must be able to locate specific locations on the fossa ovalis ("FO") reliably to safely and accurately puncture the FO septum for a given procedure. Inadvertently, puncturing structures such as the aorta, left or right atrial free wall or pulmonary vein can result in cardiac perforation and tamponade. In addition, highly specific sites on the FO must now be traversed to pinpoint specific left heart targets for device positioning.

Current transseptal procedures have specific challenges, including: (1) difficulty engaging with precision and stability on specific locations of the FO resulting from, for example, severe kyphosis, altered cardiac orientation in relation to external landmarks, abnormal cardiac rotation (secondary to multiple cardiac pathologies) and highly variable FO positions and configurations on the intra-atrial septum; (2) difficulty with needle advancement, often due to thickened or scarred septum; (3) redundant or aneurysmal septum leaving the apex of the tented needle on the FO, adjacent to the LA free wall and thus at risk for perforation and pericardial tamponade; and (4) prior septal occluder placement necessitating alternative puncture locations on the native septum or direct occluder puncture.

ABBREVIATIONS

Unless otherwise noted, the following abbreviations apply throughout the disclosure:
FO: fossa ovalis 202
Fr: French (increments for catheter sizing diameter)
GW: guide wire 10
LA: left atrium 208
LAA: left atrial appendage 210
MRI: magnetic resonance imaging
MV: mitral valve 212
RA right atrium 206
TEE: transesophageal echocardiography
TTE: transthoracic echocardiography

SUMMARY OF THE INVENTION

The present invention relates to a unique catheter system and more specifically a novel needle-guide wire 10 for use in atrial transseptal puncture with a uniquely configured needle 12 distally in continued proximity with the segmented GW 10 for catheter system device delivery. The general target for puncturing the atrial septum in the heart 200 is the FO 202, a depression on the right side of the intra-atrial septum 204 on the wall between the right atrium 206 and left atrium 208. The FO 202 is the remnant of a thin fibrous membrane that usually covers the foramen ovale during fetal development.

Specifically, the present invention is directed in part to a transseptal GW 10 incorporated with a transseptal needle 12. The GW 10 segment comprises a stiff proximal segment end 16 and a middle loop segment 14, wherein the distal end 22 comprises the junction of the transseptal needle 12. At least two mid-segment GW loops 24, 26 come to rest in the LA 208. The middle loop segment 14 is formed of a shape memory material to form at least two looped segments, the second more distal, usually outer, broad coil 24 and a first, more proximal, or inner coil 26; wherein the middle segment 14 is in continuity with the elongated linear extra-stiff GW segment 16 at proximal end 25, which eventually rests externally for exchanges.

The present invention is further directed to a transseptal GW puncture system that traverses the FO 202, comprising a proximal end 16, a distal end 22, a middle coiled segment 14, a transseptal dilator 108, and a sheath 100. The distal end of the GW puncture needle 18 comprises a transseptal needle 12 attached to the looped GW segment 14 at its distal end 22 and in turn is positioned in continuity with the distal end 17 of the linear, extra-stiff GW segment 16. The transseptal needle 12 has shape memory at the point of attachment to the looped GW segment 14 wherein the shape memory is sufficient to have the transseptal needle 12 retain a pre-specified abrupt angle with respect to the looped guide wire segment 14 to maintain atraumatic stability within and central to the loops 24, 26. One or more of the loops 24, 26 are positioned and stabilized in the LA 208 resting adjacent to the inner surface of the LA 208. The middle looped segment 14 is formed of a shape memory material to form the two loops 24, 26; wherein the proximal end 25 of the more proximal coil 24 is in continuity with the proximal elongated extra-stiff segment of the GW 16; and wherein a secondary bend 29 is positioned in the RA 206 transitioning into the elongated, linear proximal most segment of the GW 10.

The transseptal dilator 108 comprises an elongated catheter 109 which rests within the sheath 100, tapering down to a narrowed dilator distal segment 110, wherein the catheter lumen 111 throughout remains compatible with the GW 10, which may have a full spectrum of diameters ranging from 0.021 inches to 0.035 inches or more. At some point along the distal segment 106 is a radiopaque marker 122 positioned to be overlapped with the radiopaque tip marker 123 on the sheath 100 when at that point the transseptal dilator 108 and sheath 100 are of equivalent external diameters. The dilator 108 is advanced forward into a precise position of the FO 202 for "tenting" the FO 202 by way of a series of forward movements of the actuator 112 adjacent to the distal end of the handle 104. Steerable maneuvers on the proximal sheath handle 104 permit antigrade and retrograde flexion, and torqueing anterior or posterior of the entire sheath 100 will be carried out to position the distal end 124 of the sheath and the retained dilator tip 110 adjacent to the specific FO site for the specific procedure. Advancement and retraction movements of the dilator distal segment 110 relative to a stabilized sheath 100 with the use of an actuator 112 on the proximal sheath 100 interacts with the proximal end 119 of the dilator 108.

Once the FO 202 is tented with the dilator 108 which contains the transseptal needle 12, the needle 12 is advanced, puncturing the FO septum 202 and crossing into the LA 208. The transseptal needle 12 folds or bends from shape memory at a discrete angle at the proximal end/hinge point 20 on the coiled GW segment 14 to which it is connected after being advanced across the FO 202. It forms an angle which may range from about 45° to 140°. Further advancement of the transseptal GW 10 will position the looped section 14 coils of the GW 10 stable within the LA chamber 208 aiding also in preserving the needle position atraumatically in the central LA 208 by way of remaining central to the loops. Preferably, the GW coils 24, 26 have a small inner diameter coil 26 and larger outer diameter coil 24 aiding in preserving the needle 12 highly central to the LA 208. The smaller in diameter inner coils prevent excessive needle 12 damage to the tissue in the LA wall. In another embodiment, the coils 24, 26 may be of equal diameters.

Figure 1:
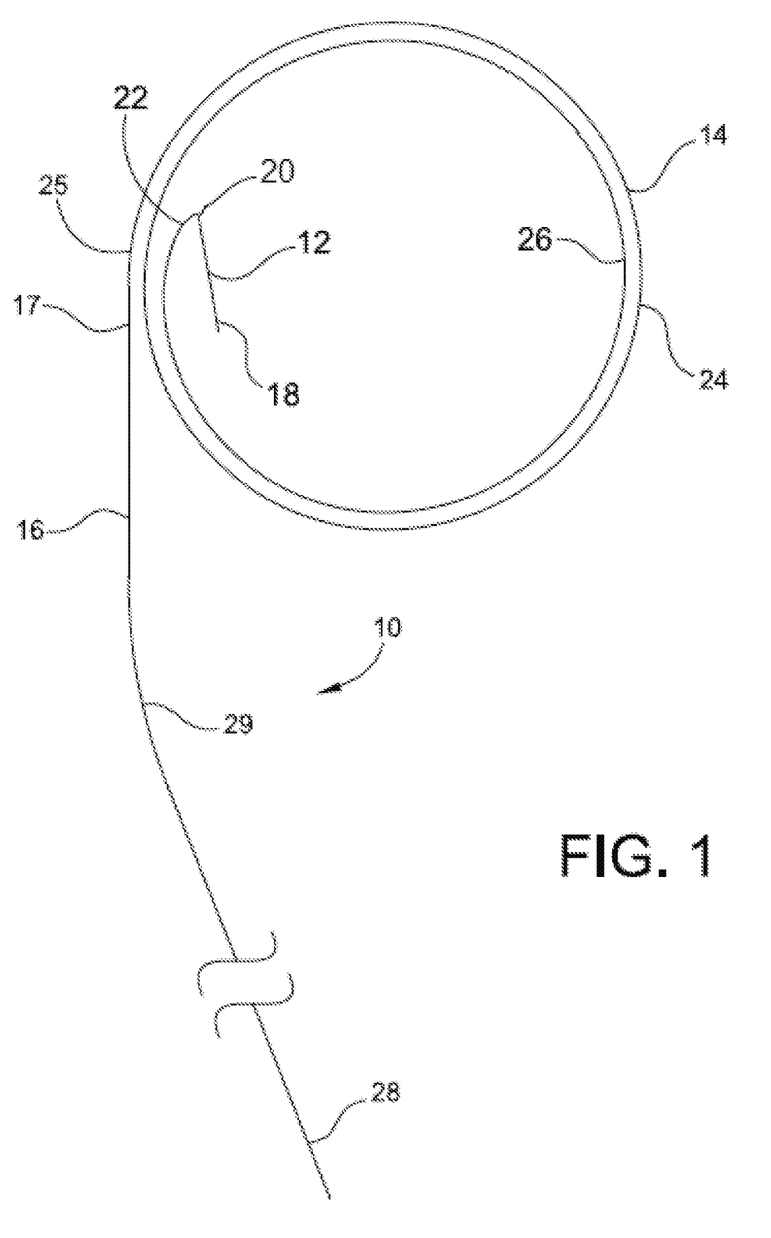
FIG. 1 is a side plan view of the first embodiment of the present invention of the combined transseptal needle and GW profiled in the frontal plane.
Figure 2:
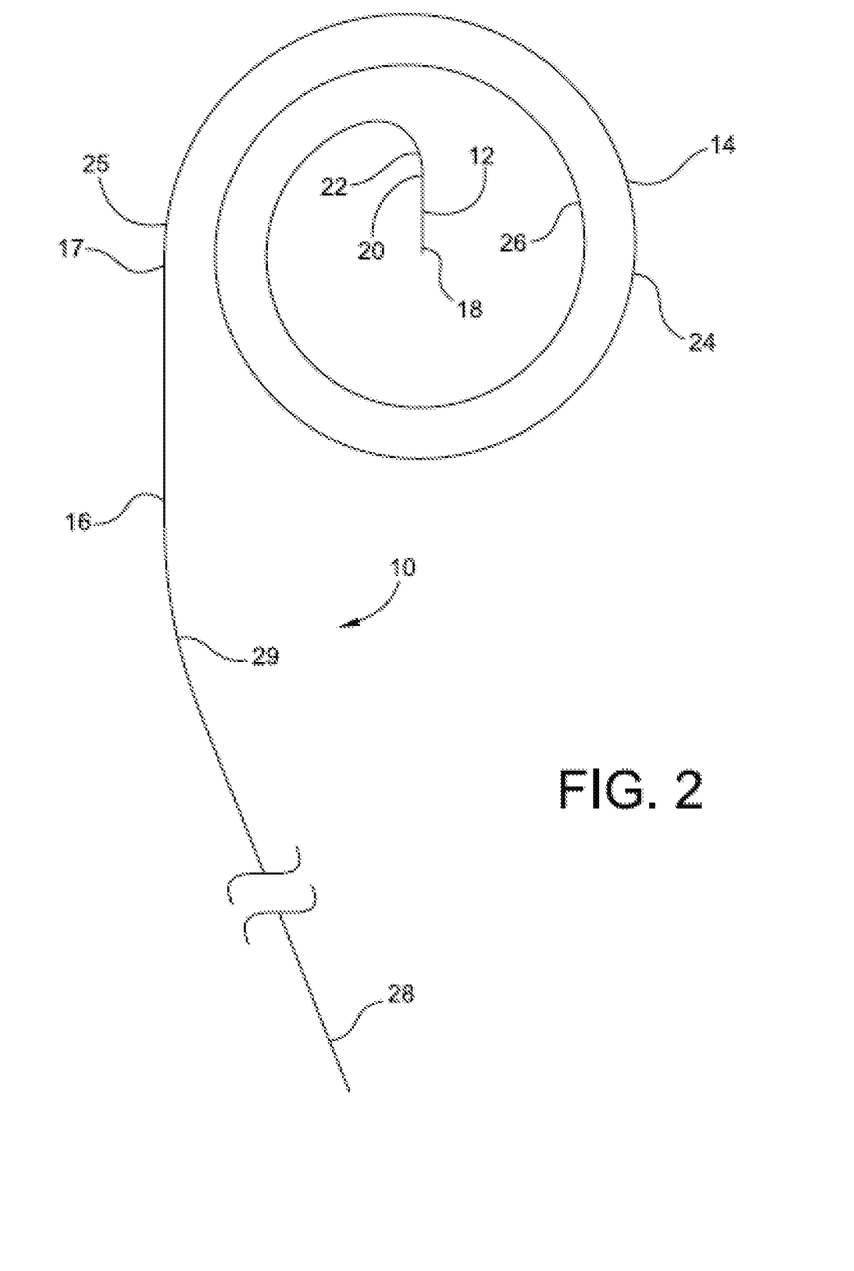
FIG. 2 is a side plan view of a second embodiment of the combined transseptal needle and GW of the present invention in the frontal plane.
Figures 3, 4:
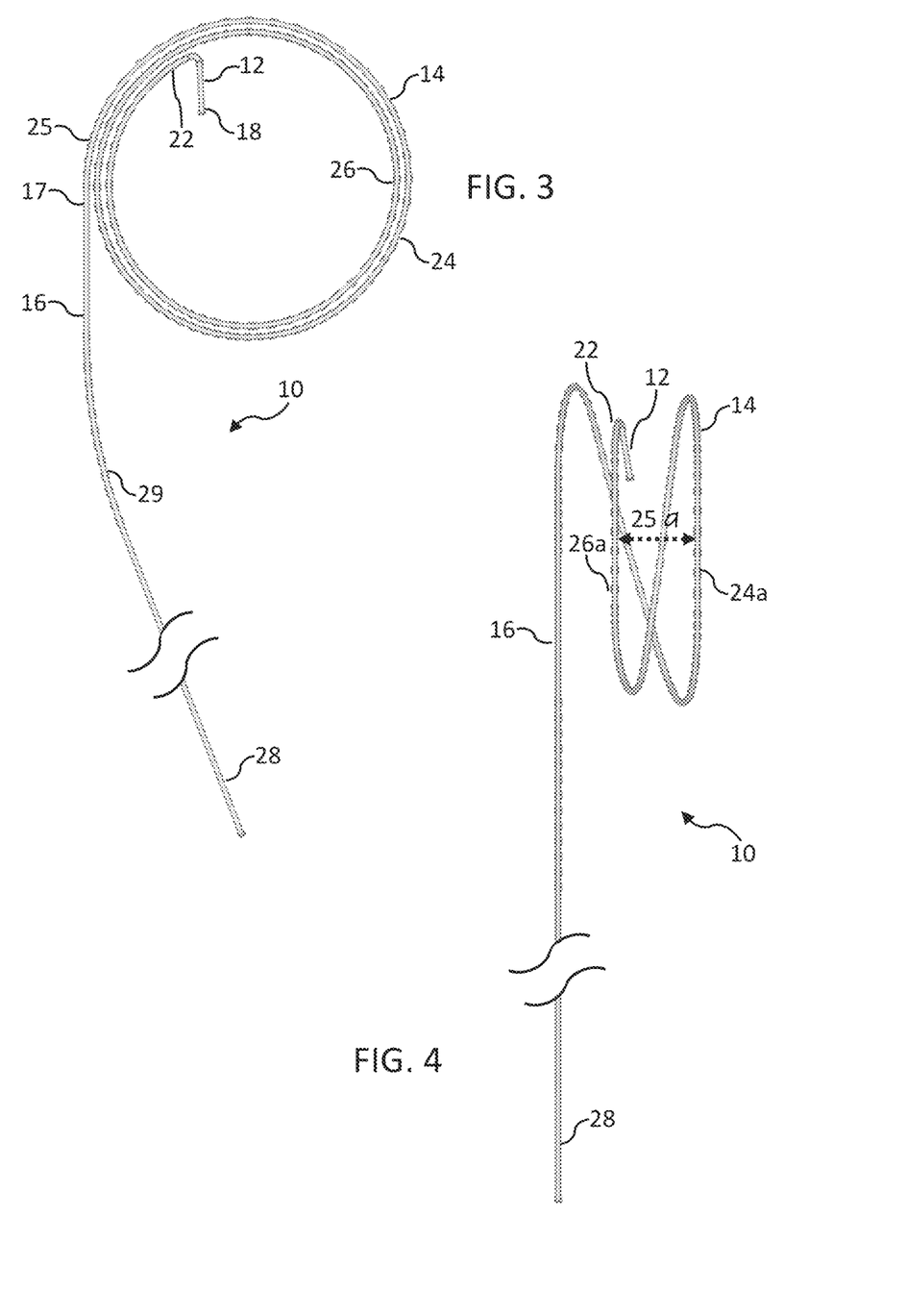
FIG. 3 is a side plan view of a third embodiment of the present invention of the combined transseptal needle and GW with offset loops viewed from a frontal planar perspective.
FIG. 4 is a front plan view of the transseptal needle of FIG. 3 which has been rotated ninety degrees.

In another embodiment, the coils 24, 26 may be offset, as illustrated in FIGS. 3 and 4, to further aid in preserving a central location of the needle 12 which can also be folded in a third dimension, an additional feature making it less susceptible to perforating LA 208 structures when the folded distal transseptal needle 12 is advanced and deflected medially further aiding in maintaining a central needle 12 position within the offset but equal spaced loops 14. Coils 24, 26 may be offset by approximately 0.75-2 cm inches. The coils 24, 26 are intermediate in stiffness allowing for less traumatic interaction with the LA free walls. A secondary bend 29 in the right atrial GW segment aids in preserving a perpendicular trajectory across the FO 202 and co-axially in the IVC 215. The elongated, proximal extra-stiff GW segment 16 will have a preferable length of 260 cm (but may be significantly longer) for purposes of catheter or device exchange.

Novel features unique to this dilator and deflectable sheath in the system include a longer extendable dilator tip in relation to the sheath. Strategic positioning by overlapping the dilator radiopaque marker 122 and sheath radiopaque marker 123 for alignment at equivalent external diameters permit smooth transitioning of the transseptal dilator 108 and sheath 100 across the membrane of FO 202.

The forward positioning of the catheter system of the present invention allows for precise positioning of the distal sheath for precise device positioning thereby establishing ideal LA 208 positioning ultimately dictated by the specific left heart target for a given device, i.e., LAA 210, MV 212. The system is intuitive and simple to accurately position on a specific FO 202 target by using iterative dilator advancement under echo or other imagining guidance. After the coils have been advanced across the FO 202 and secured in the LA 208, the dilator 108 is then advanced over the coiled GW 10 into the LA 208 preserving the overlapping radiopaque segments in place until the sheath 100 has crossed into the LA 208. Overlapping radiopaque markers 122, 123 on the distal dilator end 106 and sheath tip 124 are used to confirm that they are at equivalent diameters for smooth simultaneous advancement of the dilator 108 and sheath 100 across the FO 202.

The deflectable and steerable nature of the sheath 100 will permit the sheath 100 to obtain the directionality, angulation and reach using a single size forward looking catheter system for the variety of RA 206 sizes and FO 202 angles in various patient-specific anatomy.

The collective system preferably includes a needled GW wire 10 delivered by the "one size fits all" catheter system for iteratively advancing the dilator 108, containing the retracted needle 12, into a precise tenting position on the FO 202. An actuator 112 on the sheath 100 adjacent to the handle 104 permits highly controlled advancement of the distal segment 110 for "tenting" the FO membrane prior to needle puncture. The actuator 112 can be advanced or retracted with the operator's thumb without removing the operator's hand from the rotatable handle 104. The dilator 108 may have a more flexible distal segment to permit smooth tracking over the coiled GW segment in the LA 208. The deflectable sheath tip 124 may have monopolar or bipolar directionality. Preferably the steerable sheath 100 will have a distal fixed 2° bend within the RA 206 which may range from 2° to 20° to more easily establish perpendicularity to the FO 202. Standard, commercially available sheath dilator catheters may also be used in combination with the previously described novel needle GW.

Advantageously, the device satisfies the following: (1) improved ease of use; (2) intuitive manipulation for precise distal control; (3) improved device and procedural efficacy; (4) increased device safety across a wide range of operator skills; (5) enhanced workflow and decreased procedural times; and (6) decreased procedural costs secondary to a combined needle GW.

The objects and advantages of the invention will be highlighted in greater detail in the following description of the preferred embodiment of the invention in conjunction with the accompanying drawings.

DETAILED DESCRIPTION OF THE INVENTION

With reference to the guide number in the drawings, the transseptal puncture system of the present invention is preferably a "one size fits all" system whereby a single-sized system may be used in a variety of anatomical configurations and atrial sizes. An exception to this new standard is directed to the use of multiple wire diameters on the order of about 0.021 inches to greater that 0.035 inches. The system includes specialized components, including an exchange GW with a distal transseptal needle and adjacent coils or loops for GW securement in the LA 206. In addition, the catheter components may include a novel dilator which interacts with an actuator on the proximal sheath handle for controlled positioning on the FO aided by the steerable sheath.

The Needle-Guide Wire

Reference is made to FIGS. 1-4 illustrating a needle-guide wire 10. The transseptal needle-GW 10 should be a single component and avoid the need for a separate transseptal needle, multiple exchanges and multiple lengths and curves for various anatomies. The single wire has at least three defined segments: (1) the distal transseptal needle 12; (2) the middle or looped LA segment 14; and (3) the proximal elongated linear, extra-stiff GW segment 16.

Transseptal Needle 12

The transseptal needle 12 is positioned in continuity with the distal end 22 of the GW loop segment 14. The transseptal needle 12 is preferably relatively short, with a length between about 0.75 to about 2.0 cm. The needle 12 also should preferably have an ultra-low profile tip 18. The proximal end 20 of the needle 12 in continuity with the adjacent distal loop segment 14 is linear when retained in the central lumen 111 of the dilator tip prior to advancement.

The transseptal needle 12 has a lubricious coating to minimize resistance and a sharply tapered tip 18 to puncture and easily transition across the FO 202 (illustrated in FIG. 8) including those that may be densely scarred or aneurysmal. Inadvertent needle lurching across the FO membrane and loss of the preferred puncture site is avoided by the extra-fine point on the needle tip 18, slow iterative delivery of the forward-looking tapered transseptal dilator 108 into the FO 202 for stable positioning and "tenting" of the membrane by the dilator tip 18 which is in turn supported by a steerable transseptal sheath 100. With this forward looking system, unintended anterior or posterior, torqueing forces resulting in sliding across the FO 202 should be greatly minimized.

The transseptal needle 12 is preferably composed of a metallic material, such as stainless steel or alloy including nitinol with shape memory, and is attached to the GW loop segment 14 for example with a weld or possibly interdigitating slots which interact to form a more stable, yet flexible, union allowing the needle to fold on itself thereby avoiding puncturing the LA free wall, the pulmonary vein, etc. Other means of creating a pre-shaped angle between the needle 12 and loop segment 14 can also be conceived and utilized.

The transseptal needle 12 sharply angles at the proximal end/hinge point 20 where it connects to the distal end 22 of the looped GW segment 14 having retained a pre-specified angle central to the LA loop segment 14, thus maintaining atraumatic stability within the central LA loop segment 14, thus preventing contact and possible perforation of LA 208 structures including a pulmonary vein, LA free wall and LAA 210.

Following the wire advancement and transseptal puncture, the needle 12 abruptly flexes centrally preferably at an acute angle with the adjoined looped GW segment 14 as illustrated in FIGS. 1-4. The needle 12 remains linear after entering the LA 208 but flexes inward, preferably at an angle of about 45° to 140° relative to the distal looped GW segment 14. The diameter of the transseptal needle tip 18 can be ground down to an ultra-low profile and tapered back to conjoin the distal loop segment 14, most likely transitioning to a profile in the range of 0.021" to 0.035" or greater.

Guide Wire Loop Segment 14

The looped GW segment 14 is designed to stabilize the GW 10 position atraumatically in the LA 208 and, in addition, assists in protecting the left atrial free wall from unwanted needle puncture. Two or more looped segments 24, 26 may typically range between about 2.5 cm and 4.0 cm in diameter and formed by shape memory as it exits from the transseptal dilator 108 into the LA 208. The distal GW looped segment 14 in one embodiment would be formed by two roughly equal in size circular or possibly non-circular loops potentially in a plurality of shapes which are again formed upon deployment in the LA chamber, as illustrated in FIGS. 3-4.

The coils provide at least four useful functions:
1. The coils can confirm the correct LA chamber positioning, by taking on the unconstrained, known shape within the LA 208.
2. The coils 14 maintain stable positioning in the LA 208 to avoid inadvertent withdrawal of the GW 10 into the RA 206 or forceful needle tip 12 advancement into the LA free wall or pulmonary vein.
3. The outer broad coil 24 provides a longer GW support ramp over which the dilator 108 and sheath 100 can be advanced with less resistance into the LA 208 around the curve to facilitate catheter support.
4. The coils form an outer protective shield in which the centrally positioned needle 12 is kept at a safe distance from penetrating LA 208 structures.

In another embodiment, there are at least two circular coils, the inner coil 26 diameter being smaller than the outer coil 24 diameter, as illustrated in FIGS. 1-4, the inner coil thus central to the outer coil 24. In this embodiment, the larger, outer coil 24 can be compressed by LA 208 structures in the absence of any conformational change of the inner coil 26 thus further protecting deformity of the distal needle 12 and preserving its central location.

As an example, the inner coil 26 of the GW 10 may have a diameter between about 1.5 cm and 3.0 cm, preferably about 2.5 cm. The outer coil 24 may have a diameter between about 3.0 cm and 4.0 cm, preferably about 3.5 cm.

In a third embodiment, the two coils 24, 26 have parallel portions 24a and 26a and are unequal in diameter, but can be offset by about 0.75 cm to about 2.0 cm, which in combination with a second preformed bend at the junction of the distal transseptal needle 12 and the GW loop segment 14 in the third dimension central to the two offset wire coils 24, 26, as illustrated in FIG. 4. Its purpose is to further aid in preventing needle perforation of the LA 208 by allowing the needle 12 to not only be centered circumferentially in two dimensions upon flexion with this embodiment but the needle 12 is to be directed centrally in a third dimension between the breadth of two offset loops 24, 26. The distance between the parallel portions 24a and 26a of coils 24, 26, as illustrated by dotted line 25a, would preferably be about 1 cm, and may range from about 0.75 cm to about 2.0 cm.

Proximal Guide Wire Segment 16

The proximal GW segment 16 is in continuity with the adjacent coil segment 14 at the distal end 17 of the segment 16. The proximal GW segment 16 includes a proximal free end 28, which is exteriorized with adequate length to permit catheter or device exchange while preserving distal GW loop segment 14 positioned in the LA. The distal end 17 of this segment transitions linearly across the atrial septum into the LA 208. There is then preferably a shallow fixed second degree bend 29 roughly in the mid-RA 206, retaining a preferable angle of 2° to 20°. The elongated proximal extra-stiff GW segment 16 extends from most distal end of the long proximal segment 17 to the most proximal end 28 having a preferred diameter of 0.021" to 0.035." The long proximal extra stiff GW segment 16 may extend from 240 cm to 300 cm, preferably 260 cm in length. This long, extra stiff GW segment 16 will serve as a supportive rail for exchanging an array of catheters and devices for delivery to left heart targets.

Guide Wire Introduction Sheath 100

Figures 5, 6:
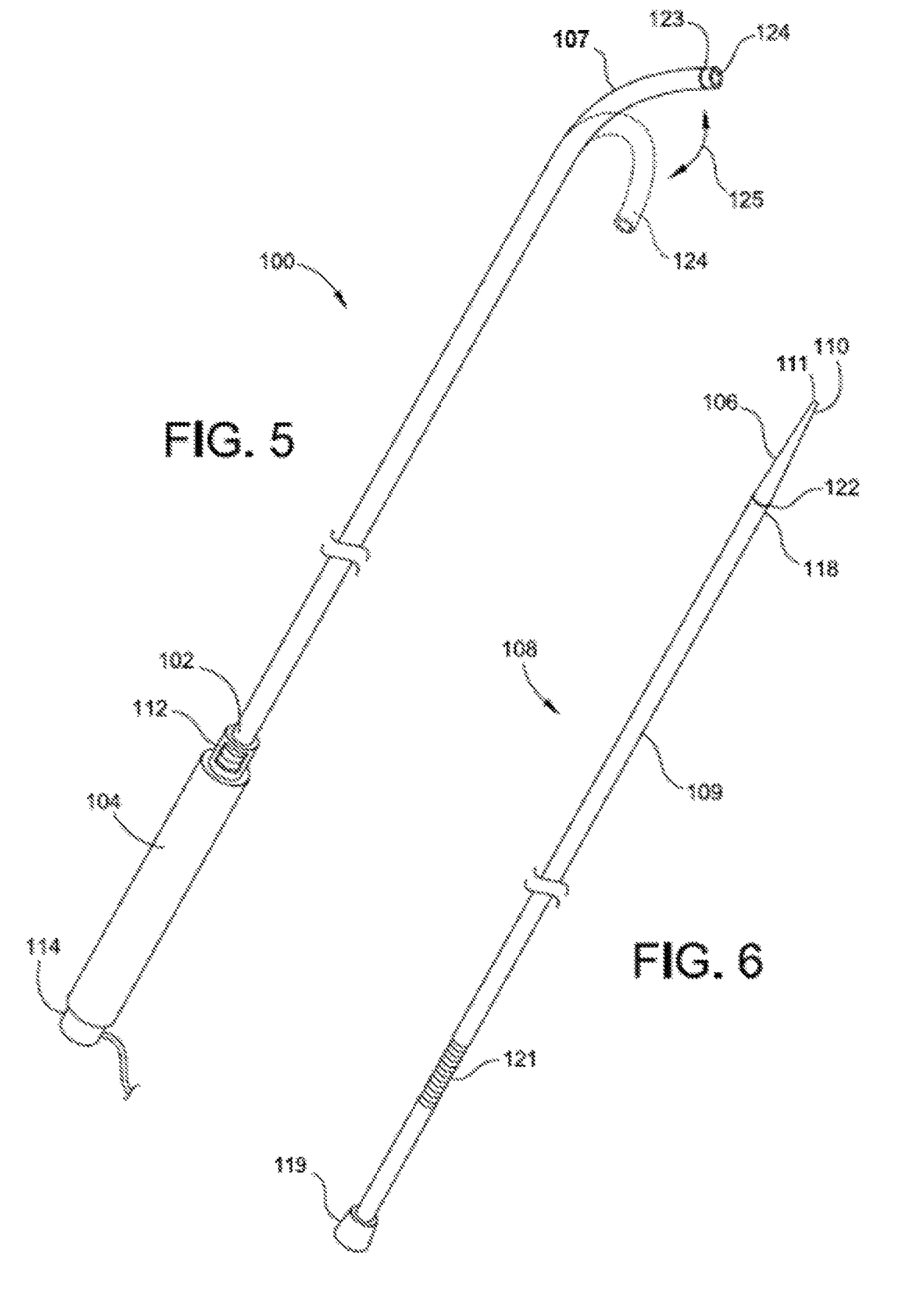
FIG. 5 is a side plan view illustrating a representative unipolar deflectable sheath for use with the needle-GW in the present invention.
FIG. 6 is a side plan view illustrating a dilator for use with the deflectable sheath of FIG. 5.

Referring to FIG. 5, the transseptal delivery sheath (or sheath) 100 is preferably a unipolar, but may be a bipolar, deflectable sheath actuated with a rotatable proximal ergonomic handle 104 for superior/inferior flexion, and one-to-one sheath torque control for optimal anterior/posterior positioning, advancement or retracting the transseptal sheath 100 permits superior and inferior positioning for controlled, atraumatic guidance in all planes. The sheath 100 has a proximal end 102 located adjacent the actuator 112 and a distal segment 107. Current transseptal systems designed for commercial use are brought into the FO 202 using a clockwise torque of the sheath/dilator system generally from a femoral vein access sight that may be overly aggressive (excessive in length) which may in turn result in inadvertent "stored up" torque if the over-reaching dilator 108 momentarily "catches" distally on an atrial septum prominent ridge. Further efforts to position the dilator distal segment 110 within the FO 202 may result in perforation of the RA 206 free wall or appendage. Conversely, a dilator 108 of insufficient length or "reach" and inability to engage the membrane across the FO 202 results in an inability to puncture the FO 202.

Multiple sheath sizes for each system must be available to accommodate variable RA sizes and configurations in these current commercially available systems. The sheath 100 has an ergonomic two-way rotatable handle 104 for superior and inferior distal sheath flexion, illustrated by arrow 125 and reach at the sheath tip 124 of the sheath 100. In addition, 1:1 torque transfer distally in an anterior to posterior position is accomplished through wire braid reinforcement (not illustrated) of the sheath 100 which also improves back up support for enhanced device delivery. The sheath 100 is initially positioned adjacent to but without engagement of the atrial septum using fluoroscopic and TEE guidance and when available, possibly real time MRI and computer tomography.

As will be illustrated shortly, once the sheath 100 is accurately positioned at the appropriate short distance from the FO 202 (probably about 0.5 to about 2.0 cm) in the RA 206 under imaging guidance, the dilator 108 is advanced while keeping the sheath 100 stationary. The sheath handle 104 and adjacent actuator 112 for the dilator will permit total system (sheath and dilator) manipulation with one hand kept in position without need for use of the operator's contralateral hand. The actuator 112 for the dilator 108 can be manipulated by the operator's thumb or other digit for iterative forward advancement or retraction by interacting with the frictional elements 121 on the dilator 108. The wire-braid, reinforced sheath 100 provides strong backup, kink-resistant support for advancing the dilator distal segment 110 of the dilator 108 and subsequently the dilator 108 into a precisely controlled specific location of the FO 202 for "tenting" of the membrane.

The sheath 100 preferably includes but will not necessitate a dilatable shaft to accommodate highly variable device profiles; on the other hand, a series of fixed diameter sheaths may be used to accommodate a variety of device profiles. Ideally expandable or dilatable sheaths, ranging from about 8.5 Fr to potentially up to 30 Fr, could eliminate the need for keeping multiple sheath diameters available for different procedures. One embodiment is thus a single sheath size which is conformed to be dilatable across a range of diameters. Transseptal sheaths which may require deflectability at two or more distances from the proximal handle may be preferred for device delivery around complex or multiple curves.

A plurality of other supportive structures may run linearly within the sheath body to preserve an adequate level of support for subsequent device delivery across more angulated anatomy. A 2° to 20° secondary bend may be positioned proximal to the more distal deflectable bend which would aid in achieving a more perpendicular angle at the FO for strong coaxial backup support. In addition, this would permit distal flexion greater than 180°, which may on occasion be needed to achieve appropriate sheath positioning within the medial aspects of the left heart. A tight hemostatic valve on the sheath hub 114 would minimize back bleeding around the GW 10, including those with diameters down to 0.021 inch. Preferably, the sheath 100 will be 90 cm long (70 cm usable length) or longer. Hubs for locking the dilator to the sheath may be incorporated.

Transseptal Dilator 108

The transseptal dilator 108 (or "dilator") preferably has an ultra-low-profile distal segment 110 with a reverse taper back, illustrated at 106, to a fixed external diameter 118 at the distal end 106 of the dilator 108, compatible with the internal sheath diameter. The dilator 108 can be advanced in a forward motion until "tenting" of the FO membrane is demonstrated in a precise position specific to the position visualized by TEE or other real time imaging detectors specific to the procedure being performed.

In a preferred embodiment, the dilator 108 will interact with the actuator 112 adjacent to the sheath handle 104 by way of a frictional contact element 121 or use of interlocking gears for precise gentle control of the dilator movements. An actuator 112 that permits advancement or retraction of the dilator will preferably be controlled with the ipsilateral thumb, preserving the ability to maneuver both the dilator 108 and sheath handle 104 with one hand. The dilator 108 has variable flexibility along its length, with a more flexible distal segment 118 to prevent excessive straightening or movement of the catheter system as it is advanced over the GW looped segment 14.

The maximum length of the dilator distal segment 106 should be able to be advanced beyond the stationary distal sheath 100, preferably up to about 5 cm, although it may be altered to extend beyond the sheath tip from about 3.0 cm up to about 8.0 cm. This allows controlled advancement of the dilator 108 across the FO 202 and into the LA 208 over the distal GW 10. After the septal puncture and advancement of the dilator 108 into the LA 208, while maintaining the sheath 104 fixed in the RA 206, there should be ample space until the radiopaque markers 122, 123 overlap in the RA 206 side of the septum following which the composite system with transseptal dilator 108 and sheath 100, having flush external diameters, are now able to be advanced into the LA 208 as a single unit.

The dilator distal segment 106 ends in a low profile tip 110 and has a radiopaque marker 122 proximal to the dilator distal segment 106 matching the profile of the radiopaque marker 123 on the sheath tip 124 rendering a point of smooth transition between the two for simultaneous advancement across the FO 202 preventing "hang-up" of the sheath tip edge on the atrial septal crossing point.

Method of Operation

Figure 7:
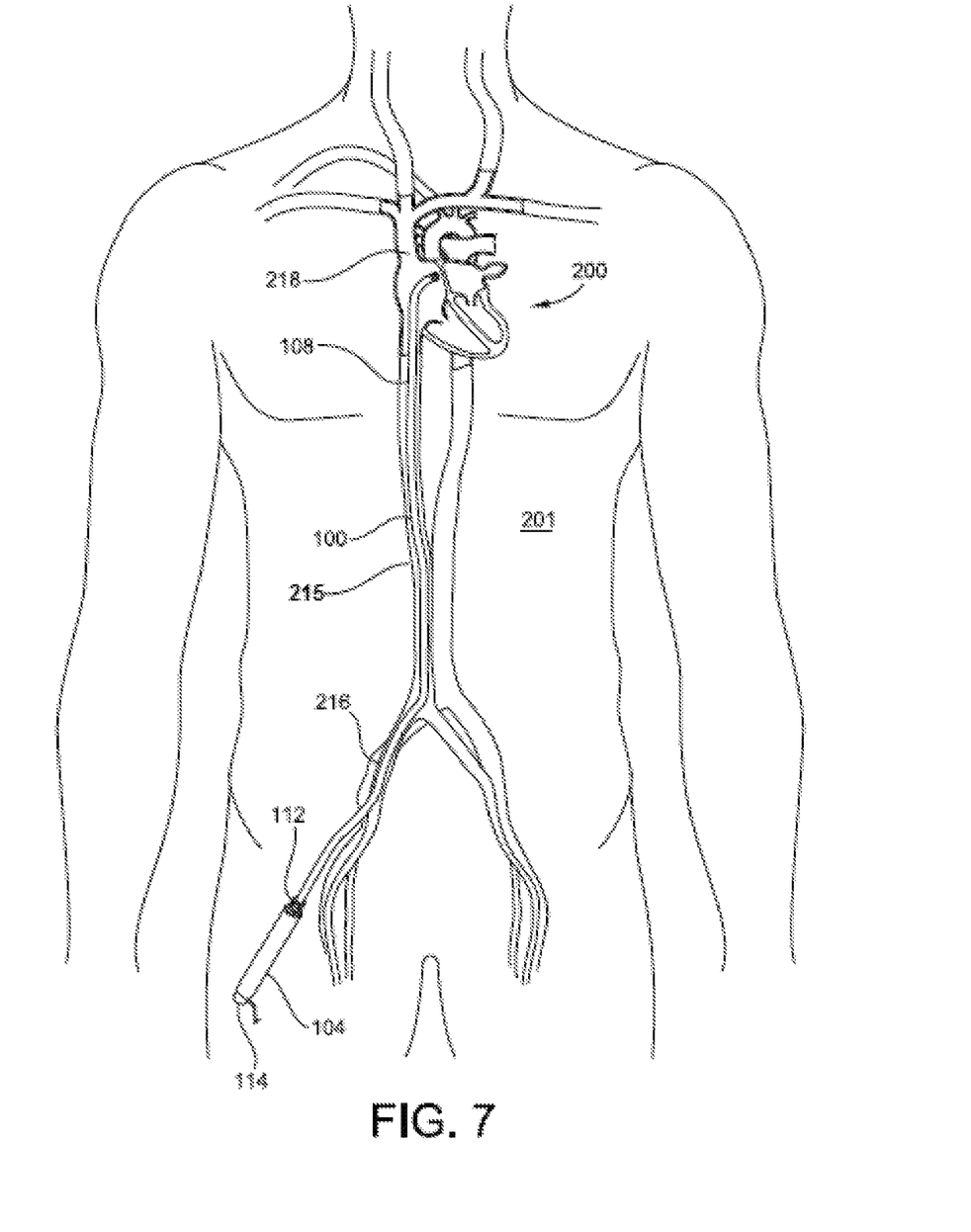
FIG. 7 is a front view schematic representation of the human central venous circulatory system including the heart and venous system with a steerable sheath present in the system.
Figure 8:
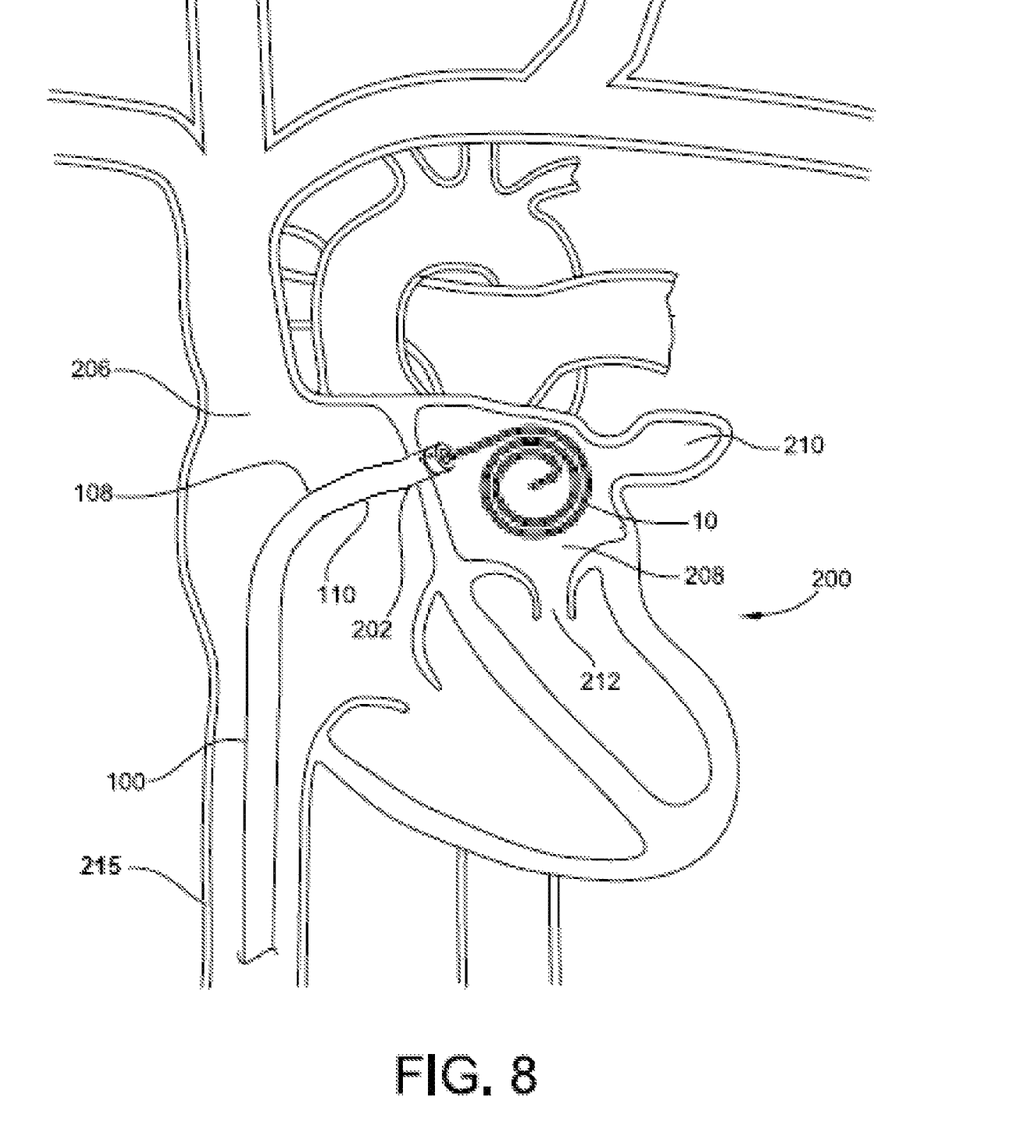
FIG. 8 is a front view schematic representation of a cross-section of the human heart with the deflectable sheath positioned across the atrial septum and positioned in the LA with the distal needle GW loops in the LA.

Referring to FIGS. 7 and 8, an exemplary method of operation is as follows on a human patient 201. As described below, this technique generally is guided by TEE or TTE supplemented with standard fluoroscopy. It should be understood that the procedure could also be guided by intracardiac echo, real-time MRI or image integration with pre-procedural volume rendered computer tomography images. This later imaging method uses standard fluoroscopic images to which the pre-acquired computer tomography images may be oriented and superimposed on for guidance. Reference is made to U.S. Pat. No. 8,900,214 to Nance et al, which is incorporated herein for a general description of human anatomy, including the heart 200, and insertion of a transseptal sheath 100 into the atrial region.

A 0.032 J-tipped GW is advanced from the right femoral vein 216 into the superior vena cava 218 using fluoroscopy. The steerable sheath 100 and dilator 108 are advanced as a unit over the J-tipped GW 10 and positioned in the mid RA 206. The J-tipped GW 10 is removed and the dilator 108 is flushed. The distal tip 18 of the GW 10 is then advanced into the 0.032 compatible dilator 108 under fluoroscopy and the distal tip 18 of the GW 10 positioned just proximal to the dilator distal segment 110.

The ergonometric handle 104 on the sheath 100 is oriented axially to permit the deflectable tip 124 to be anteflexed toward the FO 202. One to 3 cm of the dilator 108 is advanced distal to the fixed sheath 100 fluoroscopically and echocardiographically prior to maneuvering the sheath 100 toward the FO 202. To accomplish this anterior or posterior orientation, the sheath 100 is torqued anteriorly or posteriorly. The sheath 100 is advanced or withdrawn to gain a more superior or inferior position. Once again, the proximal sheath handle 104 is turned to flex the distal tip 124 to a superior, i.e., retrograde, or inferior, i.e., antigrade, trajectory. A TEE probe is most commonly used for optimal imaging of the FO 202 and adjacent dilator distal tip 110 using orthogonal views: bicaval view for superior-inferior orientation and short axis view at the aortic level to demonstrate anterior-posterior positioning. Using these TEE views, a precise position on the FO 202 for a procedure specific puncture can be obtained. The actuator 112 adjacent to the sheath handle 104 is used to slowly and iteratively advance the dilator tip 110 creating "tenting" within the FO 202 and the correct position confirmed by TEE. If the dilator distal tip 110 is incorrectly positioned, the dilator 108 can be withdrawn with the actuator 112 and redirected after manipulating the sheath 100.

With correct positioning confirmed using the tenting position, the GW 10 proximal end and the needle tip 18 punctures and crosses the FO 202 membrane. As the GW 10 is further advanced, the needle 12 flexes sharply at the hinge point 20 where it is attached to the loop segment 14 of the GW 10. As the GW 10 is still further advanced, its distal coils 14 are self-positioned in the LA 208 and the needle 12 kept flexed central to the coils 24, 26. Catheters are always aspirated and flushed with exchanges. The patient is therapeutically heparinized as soon as the GW loop segment 14 is advanced into the LA. Correct positioning of the GW 10 is confirmed by verifying its preformed shape. The coiled or looped segment 14 can take on several different embodiments as noted under the device description. The dilator 108 is advanced over the coiled wire maintaining the sheath 100 in a fixed position within the RA 206.

With the appropriate length of dilator 108 advanced under fluoroscopy, the radiopaque markers 122, 123 on the dilator 108 and sheath tip 124 come to overlap in the RA 206 confirming that the outer diameters of both catheters are equivalent and ready to be advanced into the LA 208 as a single unit. The sheath tip 124 now comes to rest across the FO 202 and in the LA 208. Again, all the dilator 108 and sheath 100 manipulations are carried out as a single-handed procedure. The dilator 108 is removed, keeping the GW wire loops 24, 26 and sheath 100 stationary in the LA 208.

The elongated proximal segment of the GW 10 is loaded with the primary device that is now advanced to the sheath tip 124 and the GW 10 is removed. The sheath 100 can then be more finely manipulated to deliver the device to the target and subsequently deployed. After deployment, the steerable sheath 100 is drawn back into the RA 206 and subsequently removed from the patient. The heparin is reversed with protamine and the percutaneous vascular entry is closed.

This transseptal procedure is carried out with a forward-looking catheter system which is iteratively advanced onto a precise position of the FO 202 prior to being punctured. The nature of the catheter system is such that only one device shape will be required to access the LA 208. This is unlike current techniques where catheters are torqued into the FO 202 using a multitude of catheter sizes which may be initially too small and unable to reach the FO 202 or too long placing the patient at risk for slipping off the FO membrane and potentially perforating the RA free wall.

Any version of any component or method step of the invention may be used with any other component or method step of the invention. The elements described herein can be used in any combination whether or not explicitly described.

All combinations of method steps as used herein can be performed in any order, unless otherwise specified or clearly implied to the contrary by the context in which the referenced combination is made.

As used herein, the singular forms "a", "an", and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference in their entirety to the same extent as if each individual reference were specifically and individually indicated as being incorporated by reference. In case of conflict between the present disclosure and the incorporated references, the present disclosure controls.

The devices, methods, compounds and compositions of the present invention can comprise, consist of, or consist essentially of the essential elements and limitations described herein, as well as any additional or optional steps, ingredients, components, or limitations described herein or otherwise useful in the art.

While this invention may be embodied in many forms, what is described in detail herein is a specific preferred embodiment of the invention. The present disclosure is an exemplification of the principles of the invention and is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting since the scope of the present invention will be limited to only the appended claims and equivalents thereof.

The scope of use for this device can be expanded for other, i.e., nontransseptal procedures, both vascular and nonvascular cavitary organ structures.

What is claimed:

1. A transseptal guide wire, comprising: a proximal end, a distal end and a middle segment,
   a. wherein the proximal end is in continuity with the middle segment via a proximal guide wire segment;
   b. wherein the distal end comprises a linear transseptal needle configured to flex from a linear puncturing arrangement to an acute angle with respect to the guide wire distal end after puncturing tissue, to maintain central atraumatic stability of the transseptal needle, and positioned in continuity with the distal end of the guide wire;
   c. wherein the middle segment is formed of a shape memory material and preformed to include at least two looped segments including an inner loop and an outer loop with the inner loop central to the outer loop in a preformed configuration; wherein the inner loop and outer loop are offset; wherein the transseptal needle is positioned between the offset inner loop and outer loop in a third dimension in addition to being circumferentially within the inner loop and outer loop in two dimensions once the middle segment returns to the preformed configuration in order to further prevent the transseptal needle from perforating tissue.

2. The transseptal guide wire of claim 1, wherein a length of the transseptal needle is between about 0.75 cm and 2.0 cm.

3. The transseptal guide wire of claim 1, wherein the transseptal needle and at least one looped segment have a lubricious coating.

4. The transseptal guide wire of claim 1, wherein the transseptal needle has shape memory at the point of attachment to the guide wire, and wherein the shape memory is sufficient to have the transseptal needle retain the acute angle with respect to the guide wire distal end to maintain central atraumatic stability.

5. The transseptal guide wire of claim 1, wherein the acute angle is about 45° with respect to the guide wire distal end.

6. The transseptal guide wire of claim 1, wherein at least one looped segment is between about 2.5 cm and 4.0 cm in diameter.

7. The transseptal guide wire of claim 1, wherein the at least two looped segments are between about 2.5 cm and 4.0 cm in diameter.

8. The transseptal guide wire of claim 1, wherein the shape memory material is nitinol.

9. The transseptal guide wire of claim 1, wherein the inner loop is offset out-of-plane from the the outer loop by a distance of about 0.75 cm to about 2.0 cm.

10. The transseptal guide wire of claim 1, wherein the proximal end has a diameter between about 0.021 inches and 0.035 inches.

11. The transseptal guide wire of claim 1, wherein the proximal end has a length between about 240 cm to 300 cm.

12. A transseptal guide wire puncture system, comprising:
    a. the transseptal guide wire of claim 1; and
    b. a transseptal dilator for placement of the transseptal needle on the fossa ovalis of a subject.

13. The transseptal guide wire puncture system of claim 12, wherein the transseptal dilator has a lumen having a diameter between about 0.021 inches and 0.035 inches.

14. The transseptal guide wire puncture system of claim 12, wherein the transseptal dilator comprises a radiopaque marker.

15. The transseptal guide wire puncture system of claim 12, further comprising a sheath.

16. The transseptal guide wire puncture system of claim 15, wherein the sheath has a unipolar or bipolar deflectable distal segment and a proximal handle for steering and positioning the unipolar or bipolar deflectable distal segment.

17. The transseptal guide wire of claim 1, wherein the inner loop has a diameter between about 1.5 cm and 3.0 cm, inclusive, and the outer loop has a diameter between about 3.0 cm and 4.0 cm.

* * * * *